(12) United States Patent
Ohno

(10) Patent No.: US 10,986,981 B2
(45) Date of Patent: Apr. 27, 2021

(54) MEDICAL IMAGING APPARATUS WITH ROTATABLE MANIPULATION RING

(71) Applicant: Sony Olympus Medical Solutions Inc., Tokyo (JP)

(72) Inventor: Atsuomi Ohno, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 253 days.

(21) Appl. No.: 15/953,749

(22) Filed: Apr. 16, 2018

(65) Prior Publication Data

US 2018/0353054 A1    Dec. 13, 2018

(30) Foreign Application Priority Data

Jun. 13, 2017    (JP) .............................. JP2017-116286

(51) Int. Cl.
| | | |
|---|---|---|
| *A61B 1/00* | (2006.01) | |
| *A61B 1/04* | (2006.01) | |
| *A61B 1/06* | (2006.01) | |
| *H04N 5/232* | (2006.01) | |
| *H04N 5/225* | (2006.01) | |

(52) U.S. Cl.
CPC ...... *A61B 1/00039* (2013.01); *A61B 1/00006* (2013.01); *A61B 1/00045* (2013.01); *A61B 1/00078* (2013.01); *A61B 1/00105* (2013.01); *A61B 1/00114* (2013.01); *A61B 1/00117* (2013.01); *A61B 1/00188* (2013.01); *A61B 1/042* (2013.01); *A61B 1/0669* (2013.01);
(Continued)

(58) Field of Classification Search
CPC ............ A61B 1/00039; A61B 1/00006; A61B 1/0045; A61B 1/00078; A61B 1/00105; A61B 1/00114; A61B 1/00117; A61B 1/00188; A61B 1/042; A61B 1/0669; H04N 5/2252; H04N 5/232; H04N 5/23216; H04N 2005/2255
See application file for complete search history.

(56) References Cited

U.S. PATENT DOCUMENTS

2003/0009084 A1*   1/2003   May .................... G02B 23/2484
                                                        600/112
2014/0275781 A1*   9/2014   Deng .................. A61B 1/00066
                                                        600/109
(Continued)

FOREIGN PATENT DOCUMENTS

JP          2006-320481         11/2006

*Primary Examiner* — Timothy J Neal
*Assistant Examiner* — William B Chou
(74) *Attorney, Agent, or Firm* — Xsensus LLP

(57) ABSTRACT

A medical imaging apparatus includes: a casing configured to form an exterior; an imaging unit housed in the casing and configured to capture a subject image; a manipulation ring rotatably provided on an outer surface of the casing; a detection unit configured to detect rotation of the manipulation ring; a manipulation calculation unit configured to calculate a rotation direction and a rotation angle of the manipulation ring based on a detection result of the detection unit; a function execution unit configured to execute a first or second function depending on the rotation direction and the rotation angle of the manipulation ring calculated by the manipulation calculation unit; and a function switch unit configured to switch a function executed by the function execution unit to the first or second function.

12 Claims, 8 Drawing Sheets

(52) U.S. Cl.
CPC ........... *H04N 5/2252* (2013.01); *H04N 5/232* (2013.01); *H04N 5/23216* (2013.01); *H04N 2005/2255* (2013.01)

(56) References Cited

U.S. PATENT DOCUMENTS

| | | | |
|---|---|---|---|
| 2015/0244937 A1* | 8/2015 | Kunishige | H04N 5/232122 348/220.1 |
| 2018/0088686 A1* | 3/2018 | Zuber | G06F 3/038 |
| 2018/0171799 A1* | 6/2018 | Moberg | E21D 9/1093 |
| 2018/0203329 A1* | 7/2018 | Takeshita | G03B 13/32 |

* cited by examiner

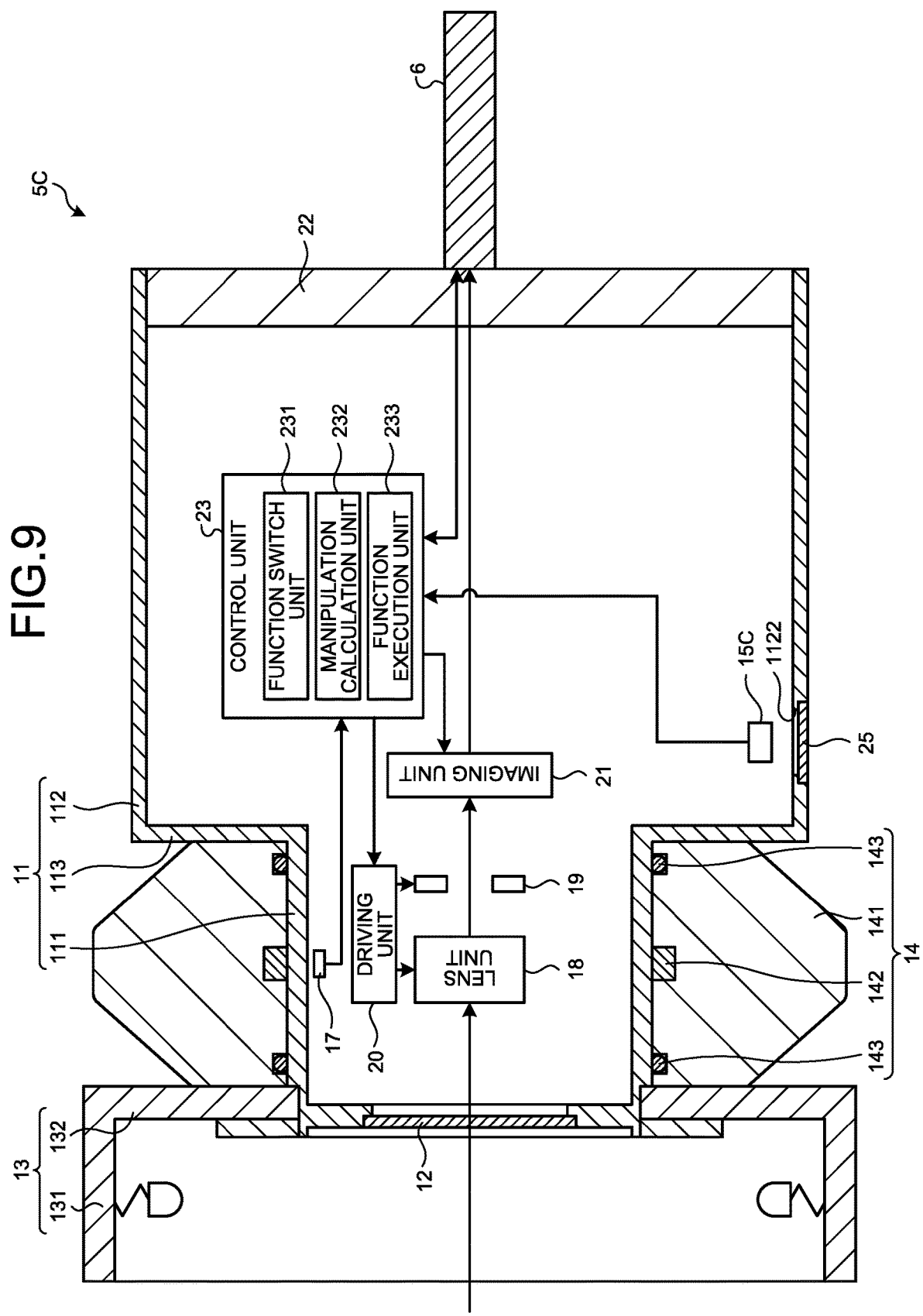

MEDICAL IMAGING APPARATUS WITH ROTATABLE MANIPULATION RING

CROSS-REFERENCE TO RELATED APPLICATION

The present application claims priority to and incorporates by reference the entire contents of Japanese Patent Application No. 2017-116286 filed in Japan on Jun. 13, 2017.

BACKGROUND

The present disclosure relates to a medical imaging apparatus.

In the related art, there is known a medical imaging apparatus having a casing that forms an exterior and an imaging unit housed in the casing to capture a subject image (for example, see JP 2006-320481 A).

The medical imaging apparatus discussed in JP 2006-320481 A (endoscope imaging apparatus) includes a manipulation ring (focus operating unit) rotatably provided on an outer surface of the casing. In addition, in this medical imaging apparatus, a focusing position of the optical system provided in the casing is changed by rotating the manipulation ring (to adjust a focus of the subject image).

Meanwhile, the manipulation ring may also be used to adjust an angle of view of the optical system (zoom in/out of the subject image), an aperture (exposure), or the like in addition to the focus adjustment. By adjusting focus, zoom, exposure, or the like in this manner using the manipulation ring, it is possible to delicately perform adjustment and improve convenience.

SUMMARY

However, when the manipulation ring is individually provided for each adjustment function of the medical imaging apparatus as described above, this degrades miniaturization and light-weight advantages of the medical imaging apparatus.

A medical imaging apparatus according to one aspect of the present disclosure includes: a casing configured to form an exterior; an imaging unit housed in the casing and configured to capture a subject image; a manipulation ring rotatably provided on an outer surface of the casing; a detection unit configured to detect rotation of the manipulation ring; a manipulation calculation unit configured to calculate a rotation direction and a rotation angle of the manipulation ring based on a detection result of the detection unit; a function execution unit configured to execute a first or second function depending on the rotation direction and the rotation angle of the manipulation ring calculated by the manipulation calculation unit; and a function switch unit configured to switch a function executed by the function execution unit to the first or second function.

BRIEF DESCRIPTION OF THE DRAWINGS

FIG. 9 is a cross-sectional view illustrating a schematic configuration of a medical imaging apparatus according to a fourth embodiment.

DETAILED DESCRIPTION

Figure 1:
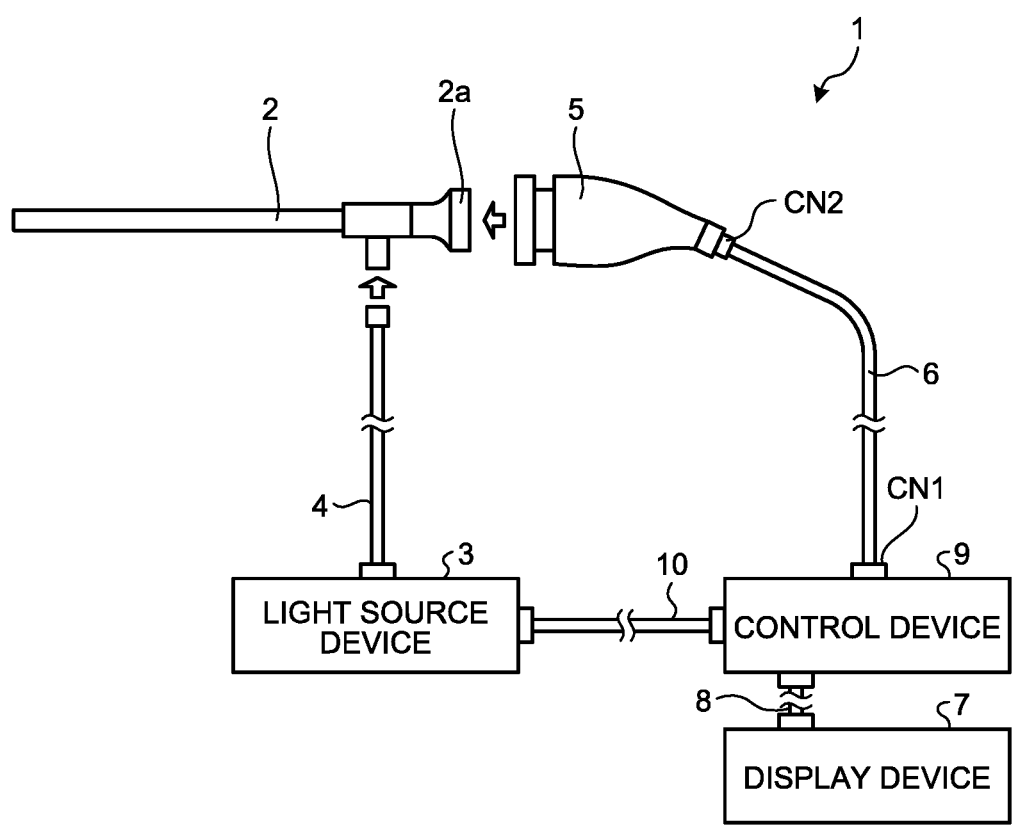
FIG. 1 is a diagram illustrating a schematic configuration of an endoscope according to a first embodiment.

Embodiments will now be described with reference to the accompanying drawings. Note that the disclosure is not limited by the embodiments described below. In the following description, like reference numerals denote like elements throughout the drawings.

First Embodiment

Schematic Configuration of Endoscope

FIG. 1 is a diagram illustrating a schematic configuration of an endoscope 1 according to a first embodiment.

The endoscope 1 is an apparatus used to observe a living body in the medical field. As illustrated in FIG. 1, the endoscope 1 includes an insertion unit 2, a light source device 3, a light guide 4, a medical imaging apparatus 5, a first transmission cable 6, a display device 7, a second transmission cable 8, a control device (controller) 9, and a third transmission cable 10.

The insertion unit 2 is a rigid endoscope. Specifically, the insertion unit 2 is formed of a rigid material or at least partially a flexible material and has a long and thin shape, so that it is inserted into a living body. The insertion unit 2 includes an optical system including one or a plurality of lenses to condense light of a subject image.

The light source device 3 is connected to one end of the light guide 4 to supply light for illuminating a living body to one end of the light guide 4 under control of the control device 9.

The light guide 4 includes one end detachably connected to the light source device 3 and the other end detachably connected to the insertion unit 2. In addition, the light guide 4 transmits the light supplied from the light source device 3 from one end to the other end to supply the light to the insertion unit 2. The light supplied to the insertion unit 2 is emitted from a distal end of the insertion unit 2 and is emitted to a living body. The light (subject image) emitted to the living body and reflected therefrom is condensed by the optical system of the insertion unit 2.

The medical imaging apparatus 5 is detachably connected to a proximal end of the insertion unit 2 (eyepiece unit 2a (FIG. 1)). In addition, the medical imaging apparatus (medical imaging sensor) 5 captures the subject image condensed by the insertion unit 2 under control of the control device 9 and outputs an image signal (raw signal) generated by the capturing. The image signal has, for example, a resolution of 4 K or higher.

Note that the configuration of the medical imaging apparatus 5 will be described below in more details.

The first transmission cable 6 includes one end detachably connected to the control device 9 through a connector CN1

(FIG. 1) and the other end detachably connected to the medical imaging apparatus 5 through a connector CN2 (FIG. 1). In addition, the first transmission cable 6 transmits an image signal or the like output from the medical imaging apparatus 5 to the control device 9 and transmits a control signal, a synchronization signal, a clock, power, and the like output from the control device 9 to the medical imaging apparatus 5.

Note that the image signal or the like transmitted from the medical imaging apparatus 5 to the control device 9 through the first transmission cable 6 may include an optical signal or an electrical signal. This similarly applies to transmission of the control signal, the synchronization signal, and the clock from the control device 9 to the medical imaging apparatus 5 through the first transmission cable 6.

The display device 7 is a liquid crystal display or an organic electroluminescence (EL) display for displaying the image based on the video signal from the control device 9 under control of the control device 9.

The second transmission cable 8 includes one end detachably connected to the display device 7 and the other end detachably connected to the control device 9. In addition, the second transmission cable 8 transmits a video signal processed by the control device 9 to the display device 7.

The control device 9 includes a central processing unit (CPU) or the like to comprehensively control operations of the light source device 3, the medical imaging apparatus 5, and the display device 7.

For example, the control device 9 applies various types of processing to the image signal obtained from the medical imaging apparatus 5 through the first transmission cable 6 to generate a video signal and outputs the video signal to the display device 7 through the second transmission cable 8. In addition, the display device 7 displays the image based on the video signal. Furthermore, the control device 9 outputs the control signal or the like to the medical imaging apparatus 5 or the light source device 3 through the first and third transmission cables 6 and 10.

The third transmission cable 10 includes one end detachably connected to the light source device 3 and the other end detachably connected to the control device 9. In addition, the third transmission cable 10 transmits the control signal from the control device 9 to the light source device 3.

Configuration of Medical Imaging Apparatus

Next, a configuration of the medical imaging apparatus 5 will be described.

Figure 2:
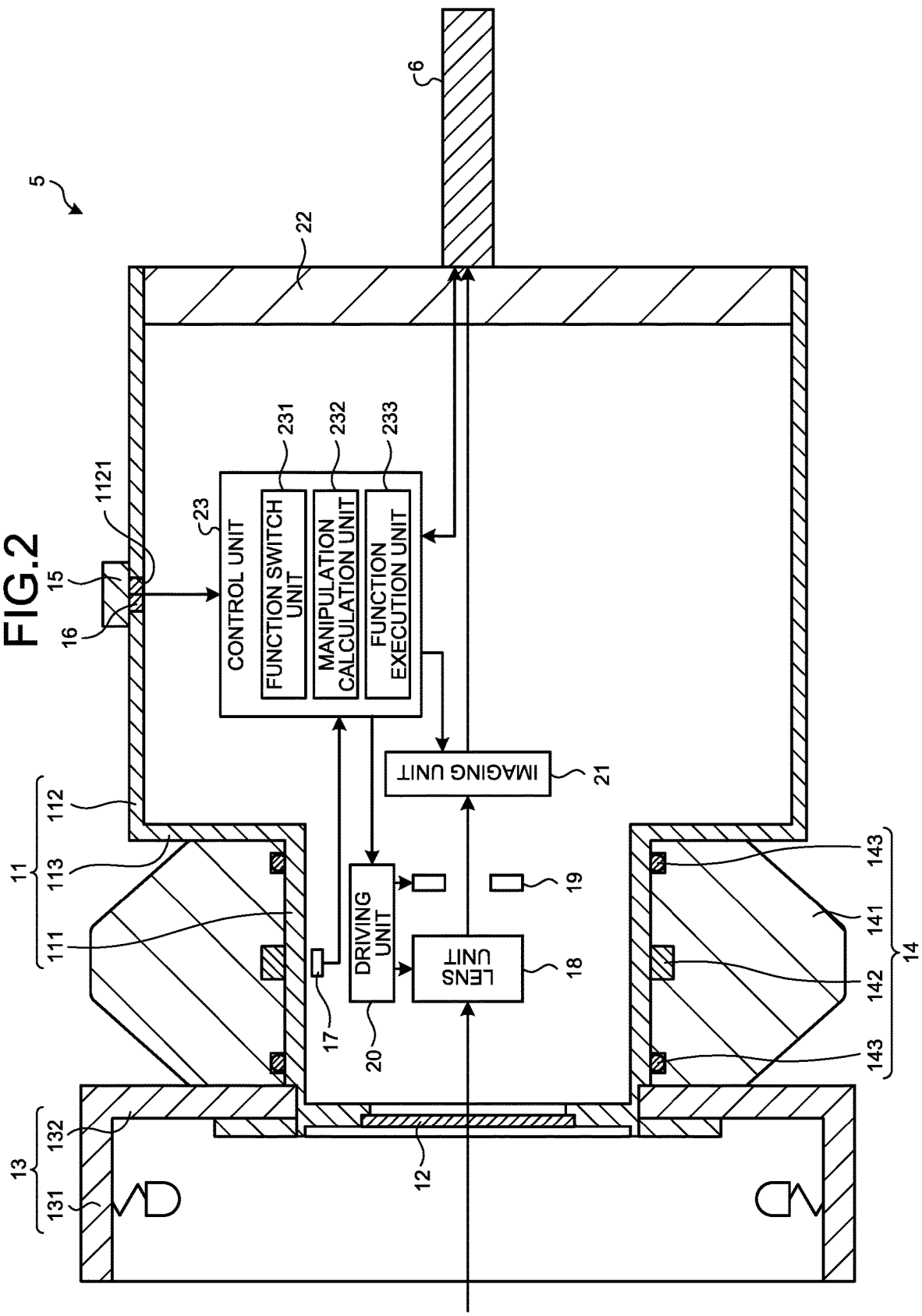
FIG. 2 is a cross-sectional view illustrating a schematic configuration of the medical imaging apparatus.

FIG. 2 is a cross-sectional view illustrating a schematic configuration of the medical imaging apparatus 5.

The terminology "distal end" described herein refers to an end portion (left end in FIG. 2) where a proximal end of the insertion unit 2 (eyepiece unit 2*a*) is connected. In addition, the terminology "proximal end" refers to an end portion (right end in FIG. 2) where the first transmission cable 6 is connected. Note that the connector CN2 of the first transmission cable 6 is not illustrated in FIG. 2 for simplicity purposes.

As illustrated in FIG. 2, the medical imaging apparatus 5 includes a casing 11, an optical element 12, a mount member 13, a manipulation ring 14, a manipulation receiving unit 15, a first hermetic connector 16, a Hall element 17, a lens unit 18, an iris 19, a driving unit (driver) 20, an imaging unit (image sensor) 21, a second hermetic connector 22, and a control unit (controller) 23.

The casing 11 is a portion that forms an exterior to house each member 17 to 21 and 23. The casing 11 is formed of a material that does not block a magnetic field such as titanium. The casing 11 includes first and second tubular portions 111 and 112 and a coupling portion 113 as illustrated in FIG. 2.

The first tubular portion 111 is formed in a cylindrical shape and is positioned in a distal end side. In addition, the first tubular portion 111 holds the optical element 12 in a distal end part on an inner circumferential surface.

The second tubular portion 112 is formed in a cylindrical shape having an inner size larger than an outer size of the first tubular portion 111 and is located in the proximal end side.

The coupling portion 113 having a ring shape is placed between the first and second tubular portions 111 and 112.

The first and second tubular portions 111 and 112 and the coupling portion 113 are integrally formed such that their center axes are aligned with each other.

The optical element 12 is fixed to the inside of the first tubular portion 111 by brazing to seal an opening of the casing 11 of the distal end side in an airtight manner. The optical element 12 is formed in a flat plate shape and is formed of, for example, sapphire glass.

The mount member 13 is a member for mounting the medical imaging apparatus 5 to the insertion unit 2 and includes a cylindrical portion 131 and a coupling portion 132 as illustrated in FIG. 2.

The cylindrical portion 131 has a cylindrical shape having an inner size slightly larger than an outer size of the eyepiece unit 2*a*.

The coupling portion 132 has a ring shape and is integrally formed in a proximal end side of the cylindrical portion 131. In addition, the coupling portion 132 is mounted to an outer circumferential surface of the first tubular portion 111 while the first tubular portion 111 is inserted.

Furthermore, the medical imaging apparatus 5 is mounted to the insertion unit 2 as the eyepiece unit 2*a* is fitted to the mount member 13.

Figure 3:
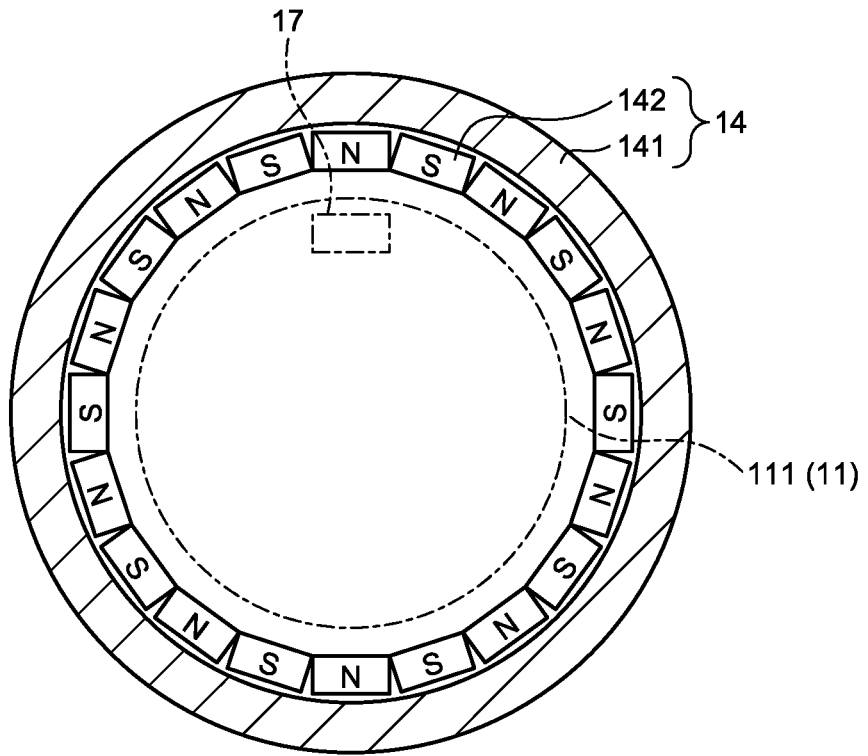
FIG. 3 is a cross-sectional view illustrating a schematic configuration of a manipulation ring.

FIG. 3 is a schematic diagram illustrating a schematic configuration of the manipulation ring 14. Note that FIG. 3 is obtained by viewing the manipulation ring 14 from the distal end side.

The manipulation ring 14 is a part manipulated by a user such as an operator and includes a ring body 141 and a permanent magnet 142 as illustrated in FIG. 2.

The ring body 141 has a ring shape having an inner size slightly larger than an outer size of the first tubular portion 111 and has a length of a center axis direction slightly shorter than a distance between the coupling portions 113 and 132. In addition, the ring body 141 is rotatably mounted to the outer circumferential surface of the first tubular portion 111 between the coupling portions 113 and 132.

The permanent magnet 142 has a ring shape having an outer size substantially equal to the inner size of the ring body 141 and is mounted to the inner circumferential surface of the ring body 141. That is, the permanent magnet 142 is rotated in synchronization with the ring body 141 in response to a user manipulation. As illustrated in FIG. 3, the permanent magnet 142 includes N-pole magnets and S-pole magnets arranged alternately along a circumferential direction of the permanent magnet 142.

As illustrated in FIG. 2, a pair of O-rings 143 for filling a gap between the ring body 141 and the first tubular portion 111 is installed in both sides that interpose the permanent magnet 142 on the inner circumferential surface of the ring body 141. That is, the permanent magnet 142 is sealed with a pair of O-rings 143 in a watertight manner.

The manipulation receiving unit 15 is a part that receives a user manipulation from an operator or the like and is mounted to an outer surface of the second tubular portion 112. According to the first embodiment, the manipulation receiving unit 15 is a push button switch.

Although not illustrated specifically in the drawings, the first hermetic connector 16 includes a tubular outer shell, an insulating plate body that blocks the inside of the output shell, and a conductive pin that penetrates the plate body. In addition, the first hermetic connector 16 is bonded between the inner surface of a through-hole 1121 and the outer circumferential surface of the outer shell by brazing or welding while it is fitted to the through-hole 1121 that penetrates the second tubular portion 112, so that the first hermetic connector 16 is fixed to the second tubular portion 112. That is, the through-hole 1121 is sealed with the first hermetic connector 16 in an airtight manner.

The manipulation receiving unit 15 is electrically connected to the conductive pin of the first hermetic connector 16 by soldering or the like. Similarly, the control unit 23 is also electrically connected to the conductive pin by soldering or the like. That is, a manipulation signal from the manipulation receiving unit 15 in response to a user manipulation is output to the control unit 23 through the conductive pin.

The Hall element 17 is a part that detects rotation of the manipulation ring 14 and corresponds to a detection unit according to this disclosure. As illustrated in FIG. 2 or 3, the Hall element 17 is placed to face the permanent magnet 142 inside the casing 11 to detect a magnetic field generated from the permanent magnet 142. In addition, the Hall element 17 outputs two-phase signals (analog signals) having different phases as a result of the detection. Note that the Hall element 17 may be a single sensor that outputs the two-phase signals or two sensors including a sensor 171 that outputs one of the two-phase signals (hereinafter, referred to as an "A-phase signal") (refer to FIG. 5) and a sensor 172 that outputs the other signal (hereinafter, referred to as a "B-phase signal") (refer to FIG. 5). When the Hall element 17 includes two sensors, the two sensors 171 and 172 are respectively placed in a position where magnetic fields having the same magnetic pole may be simultaneously detected and a position where magnetic fields having different magnetic poles may be simultaneously detected (refer to FIG. 5).

The lens unit 18 is provided inside the casing 11 and includes one or a plurality of lenses movable along an optical axis. In addition, the lens unit 18 focuses the light of the subject image condensed by the insertion unit 2 on a focal plane of the imaging unit 21. In addition, the lens unit 18 includes an optical zoom mechanism (not illustrated) for changing an angle of view by moving one or a plurality of lenses or a focus mechanism (not illustrated) for changing a focal point.

The iris 19 is provided inside the casing 11 to adjust exposure by limiting an incident amount of the light condensed by the lens unit 18.

The driving unit 20 is provided inside the casing 11 to change an angle of view or a focal point of the lens unit 18 by operating the optical zoom mechanism or the focus mechanism described above under control of the control unit 23. In addition, the driving unit 20 adjusts the light amount incident to the imaging unit 21 by driving the iris 19 under control of the control unit 23.

Note that, although the same control unit 23 and the same driving unit 20 are employed to operate the lens unit 18 and the iris 19 described above in the first embodiment, the disclosure is not limited thereto. For example, the control unit 23 and the driving unit 20 may be provided in each of the lens unit 18 and the iris 19. Alternatively, only one of the control unit 23 and the driving unit 20 may be provided in each of the lens unit 18 and the iris 19.

The imaging unit 21 is provided inside the casing 11 to capture a living body. The imaging unit 21 includes a sensor chip formed by integrating an image sensor (not illustrated) such as a charge coupled device (CCD) or a complementary metal oxide semiconductor (CMOS) that receives the light of the subject image condensed by the insertion unit 2 and focused by the lens unit 18 and converts it into an electrical signal, a signal processing unit (not illustrated) that performs a signal processing (such as A/D conversion) for the electrical signal (analog signal) from the image sensor to output an image signal, and the like. The imaging unit 21 outputs the image signal (digital signal) subjected to the A/D conversion. Note that the aforementioned signal processing unit may not be integrated with the image sensor, but may be provided separately from the image sensor.

Although not illustrated specifically, the second hermetic connector 22 includes a tubular outer shell, an insulating plate body that blocks the inside of the outer shell, and a plurality of conductive pins that penetrate the plate body. In addition, the outer circumferential surface of the outer shell of the second hermetic connector 22 is fixed to the proximal end side of the inner circumferential surface of the second tubular portion 112 by brazing or welding to seal an opening of the proximal end side of the casing 11 in an airtight manner.

Note that, when the casing 11 and the first and second hermetic connectors 16 and 22 (outer shells) are fixed to each other by welding, they are preferably formed of the same material.

The connector CN2 of the first transmission cable 6 is connected to the second hermetic connector 22. That is, the image signal (raw (digital) signal) output from the imaging unit 21 is output to the first transmission cable 6 through the second hermetic connector 22 and the connector CN2. In addition, the control signal or the like output from the control device 9 are output to electronic parts (such as the control unit 23) inside the casing 11 through the first transmission cable 6, the connector CN2, and the second hermetic connector 22.

The control unit 23 includes a CPU or the like to comprehensively control the operation of the medical imaging apparatus 5 in response to a user manipulation of the manipulation ring 14 or the manipulation receiving unit 15, a control signal from the control device 9, or the like. As illustrated in FIG. 2, the control unit 23 includes a function switch unit 231, a manipulation calculation unit 232, and a function execution unit 233.

The function switch unit 231 switches a function executed by the function execution unit 233 to a first or second function in response to the manipulation signal output from the manipulation receiving unit 15. For example, the function switch unit 231 switches the function executed by the function execution unit 233 to the first function if the manipulation receiving unit 15 including a push button switch is turned on. Otherwise, if the manipulation receiving unit 15 is turned off, the function switch unit 231 switches the function executed by the function execution unit 233 to the second function.

Figure 4:
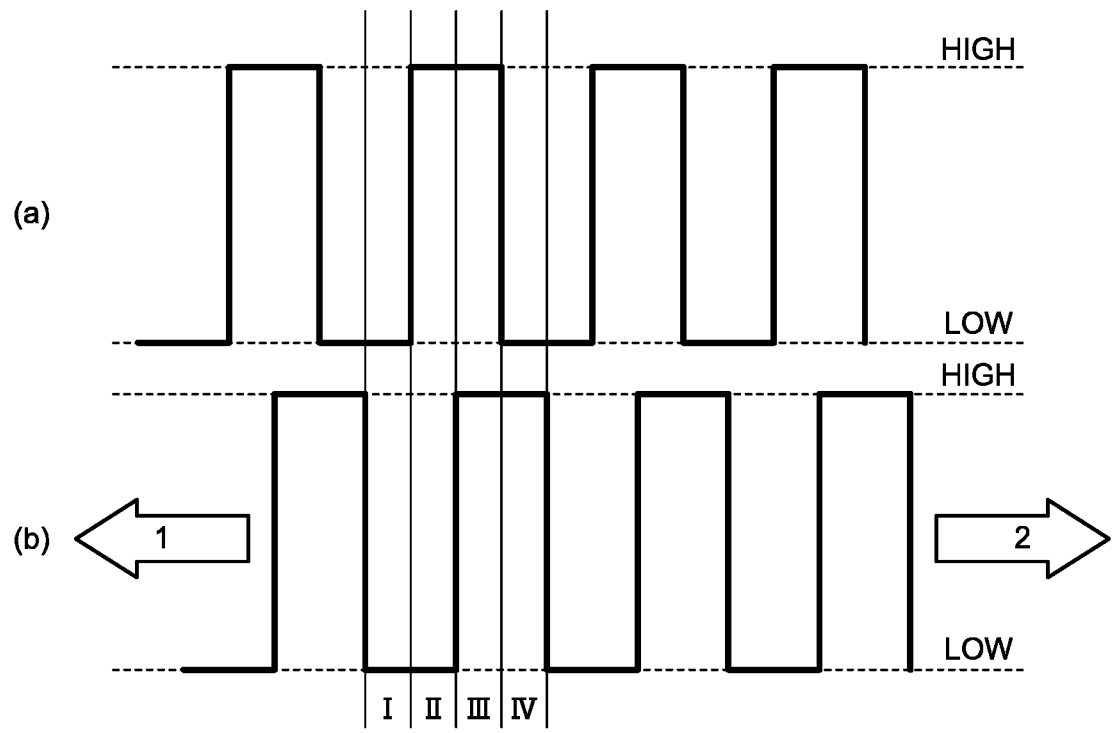
FIG. 4 is a diagram illustrating functions of a manipulation calculation unit.
Figure 5:
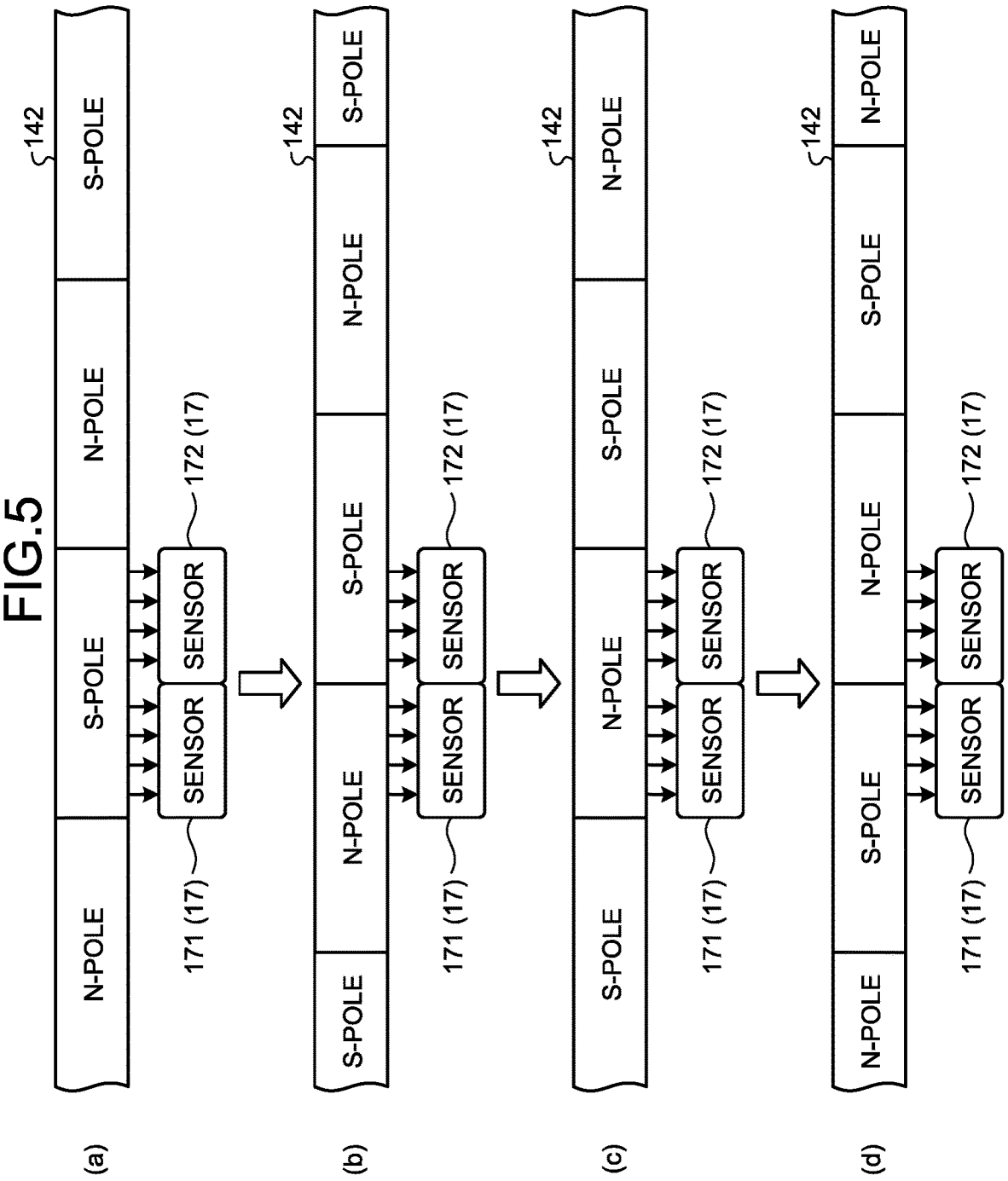
FIG. 5 is a diagram illustrating functions of the manipulation calculation unit.

FIGS. 4 and 5 are diagrams illustrating the functions of the manipulation calculation unit 232. Specifically, FIG. 4(a) illustrates a digital signal obtained by converting the A-phase signal (analog signal) output from the Hall element 17 using the manipulation calculation unit 232. FIG. 4(b)

illustrates a digital signal obtained by converting the B-phase signal (analog signal) output from the Hall element 17 using the manipulation calculation unit 232. A part (a) of FIG. 5 illustrates a position relationship between the permanent magnet 142 and the Hall element 17 in which the A-phase signal and the B-phase signal are converted into a digital signal "I" of FIG. 4. A part (b) of FIG. 5 illustrates a position relationship between the permanent magnet 142 and the Hall element 17 in which the A-phase signal and the B-phase signal are converted into a digital signal "II" of FIG. 4. A part (c) of FIG. 5 illustrates a position relationship between the permanent magnet 142 and the Hall element 17 in which the A-phase signal and the B-phase signal are converted into a digital signal "III" of FIG. 4. A part (d) of FIG. 5 illustrates a position relationship between the permanent magnet 142 and the Hall element 17 in which the A-phase signal and the B-phase signal are converted into a digital signal "IV" of FIG. 4.

Note that, although FIG. 4 illustrates a case where the A-phase signal and the B-phase signal have a phase difference of 90° by way of example, a phase difference between the two-phase signals output from the Hall element 17 is not limited to "90°". In addition, although FIG. 5 illustrates a case where the Hall element 17 includes two sensors 171 and 172 by way of example, the Hall element 17 may include a single sensor without a limitation.

The manipulation calculation unit 232 calculates a rotation direction and a rotation angle of the manipulation ring 14 based on a detection result of the Hall element 17.

Specifically, the manipulation calculation unit 232 includes, for example, a comparator to convert the A-phase signal (analog signal) output from the Hall element 17 into a High-level signal or a Low-level signal (FIG. 4(a)). Similarly, the manipulation calculation unit 232 converts the B-phase signal output from the Hall element 17 into a High-level signal or a Low-level signal (FIG. 4(b)).

The manipulation calculation unit 232 specifies the rotation direction of the manipulation ring 14 (permanent magnet 142) as a direction "1" of FIG. 4, for example, if the A-phase signal (digital signal) having the state "I" or "III" of FIG. 4 is changed from the Low-level to the High-level or from the High-level to the Low-level in advance of the B-phase signal (digital signal). Reversely, for example, if the B-phase signal (digital signal) having the state "I" or "III" of FIG. 4 is changed from the Low-level to the High-level or from the High-level to the Low-level in advance of the A-phase signal (digital signal), the manipulation calculation unit 232 specifies the rotation direction of the manipulation ring 14 (permanent magnet 142) as a direction "2" of FIG. 4.

Note that, although the state "I" or "III" of FIG. 4 is used as a reference point in the aforementioned example, the manipulation calculation unit 232 may specify the rotation direction based on a signal having a signal level changed in advance even when the state "II" or "IV" of FIG. 4 is used as a reference point.

The manipulation calculation unit 232 calculates the rotation angle of the manipulation ring 14 (permanent magnet 142) based on a change frequency of the signal level of the A-phase signal (digital signal) or the B-phase signal (digital signal).

The function execution unit 233 executes a first or second function depending on the rotation direction and the rotation angle of the manipulation ring 14 calculated by the manipulation calculation unit 232.

For example, the first function may include focus adjustment (focal point adjustment of the lens unit 18). In addition, when the function switch unit 231 switches to the first function, and the rotation direction of the manipulation ring 14 is set to the direction "1" in FIG. 4, the function execution unit 233 moves the focal point position of the lens unit 18 to a near point side depending on the rotation angle of the manipulation ring 14 by controlling the operation of the driving unit 20. Meanwhile, when the rotation direction of the manipulation ring 14 is set to the direction "2" in FIG. 4, the function execution unit 233 moves the focal point position of the lens unit 18 to a far point side depending on the rotation angle of the manipulation ring 14 by controlling the operation of the driving unit 20.

For example, the second function may include exposure adjustment (exposure adjustment using the iris 19). In addition, when the function switch unit 231 switches to the second function, and the rotation direction of the manipulation ring 14 is set to the direction "1" in FIG. 4, the function execution unit 233 reduces a maximum aperture value of the aperture (brighten the subject image) using the iris 19 depending on the rotation angle of the manipulation ring 14 by controlling the operation of the driving unit 20. Meanwhile, when the rotation direction of the manipulation ring 14 is set to the direction "2" in FIG. 4, the function execution unit 233 increases the maximum aperture value of the aperture (darken the subject image) using the iris 19 depending on the rotation angle of the manipulation ring 14 by controlling the operation of the driving unit 20.

It is possible to obtain the following effects according to the first embodiment described above.

In the medical imaging apparatus 5 according to the first embodiment, when the function switch unit 231 switches the function executed by the function execution unit 233 to the first function, the function execution unit 233 executes the first function (such as focus adjustment) depending on the rotation direction and the rotation angle of the manipulation ring 14 calculated by the manipulation calculation unit 232 as the manipulation ring 14 is rotated. In addition, when the function switch unit 231 switches the function executed by the function execution unit 233 to the second function, the function execution unit 233 executes the second function (such as exposure adjustment) depending on the rotation direction and the rotation angle of the manipulation ring 14 calculated by the manipulation calculation unit 232 as the manipulation ring 14 is rotated. That is, at least two functions (such as focus adjustment and exposure adjustment) may be executed using a single manipulation ring 14.

Therefore, since it is not necessary to provide a plurality of manipulation rings, it is possible to facilitate miniaturization and reduce a weight of the medical imaging apparatus 5. In addition, since at least two functions are executed by the manipulation ring 14, it is possible to perform delicate adjustment and improve convenience.

In the medical imaging apparatus 5 according to the first embodiment, the function switch unit 231 switches the function executed by the function execution unit 233 to the first or second function in response to a user manipulation on the manipulation receiving unit 15 including a push button switch. For this reason, it is possible to simplify a structure of the medical imaging apparatus 5.

Second Embodiment

Next, a second embodiment will be described.

In the following description, like reference numerals denote like elements as in the first embodiment, and they will not be described repeatedly.

Figure 6:
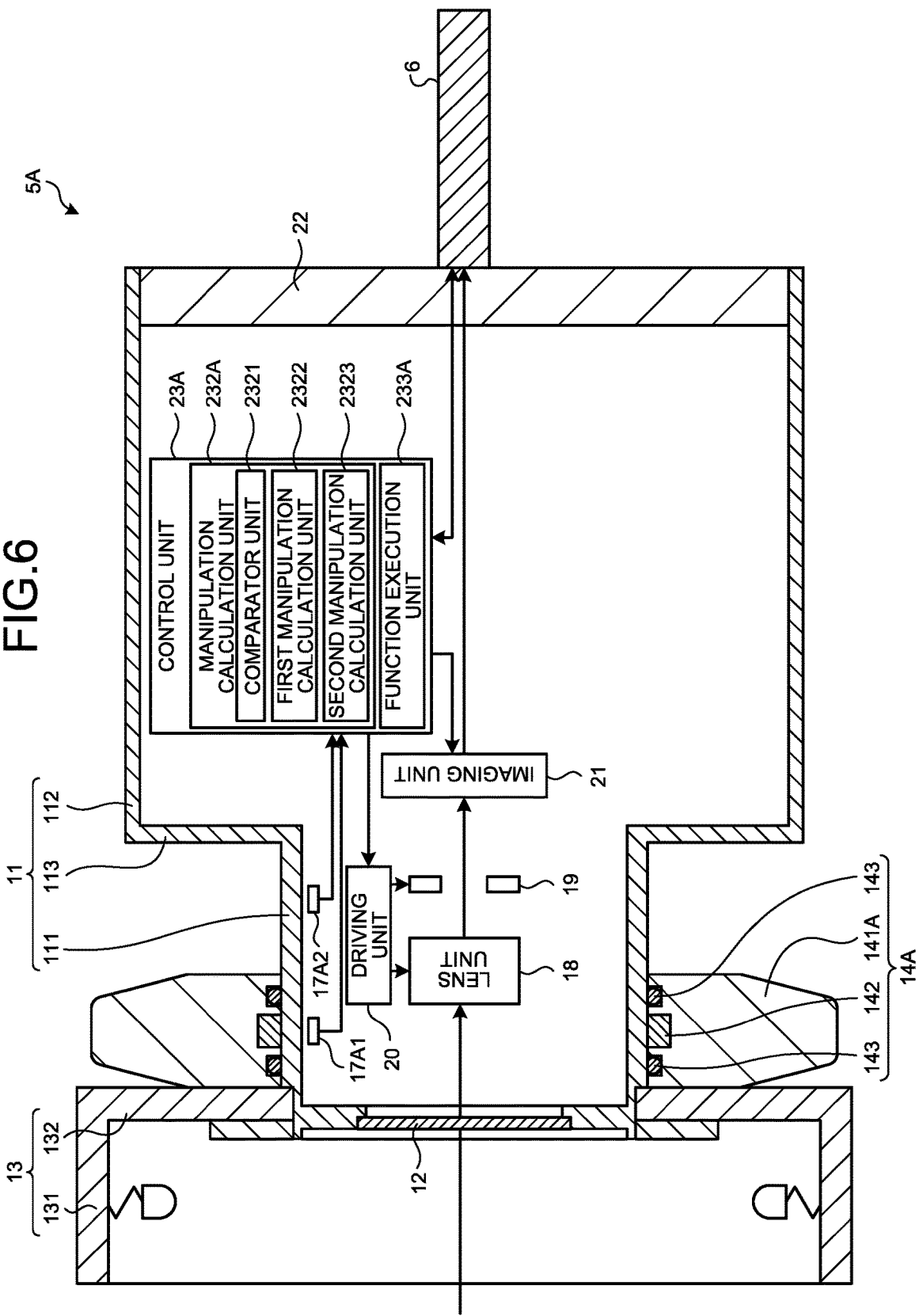
FIG. 6 is a cross-sectional view illustrating a schematic configuration of a medical imaging apparatus according to a second embodiment.
Figure 7:
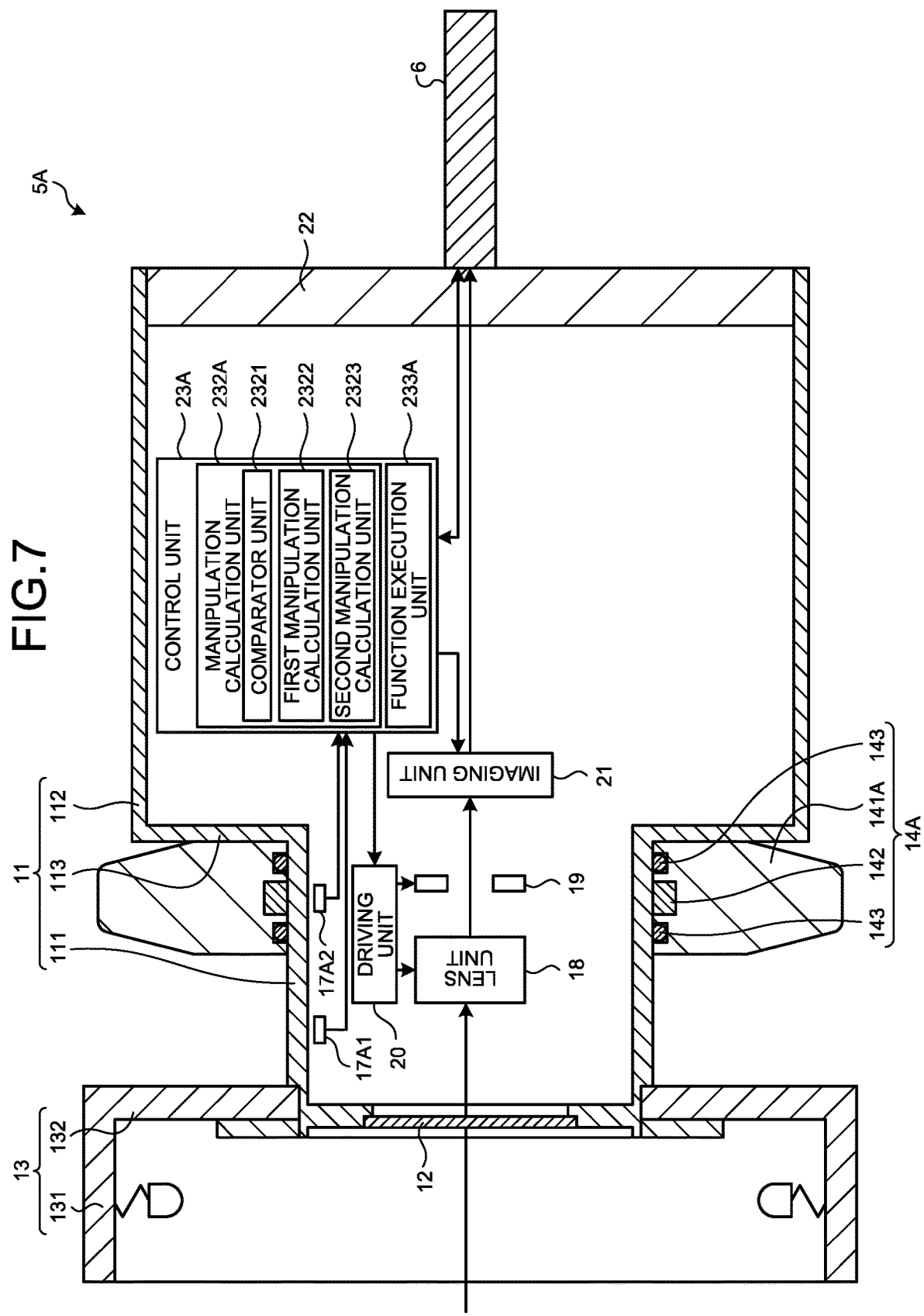
FIG. 7 is a cross-sectional view illustrating a schematic configuration of the medical imaging apparatus according to the second embodiment.

FIGS. 6 and 7 are diagrams illustrating a schematic configuration of a medical imaging apparatus 5A according to the second embodiment. Specifically, FIG. 6 illustrates a state in which a manipulation ring 14A moves to the first position. FIG. 7 illustrates a state in which the manipulation ring 14A moves to the second position.

In the medical imaging apparatus 5 of the first embodiment described above, the function switch unit 231 switches the function executed by the function execution unit 233 to the first or second function in response to a user manipulation on the manipulation receiving unit 15.

In comparison, in the medical imaging apparatus 5A according to the second embodiment, the function of the function switch unit according to the disclosure is provided in the manipulation ring 14A (FIGS. 6 and 7). In addition, in the medical imaging apparatus 5A, the manipulation receiving unit 15, the through-hole 1121, and the first hermetic connector 16 described above in the first embodiment are omitted as illustrated in FIG. 6 or 7.

Specifically, similarly to the manipulation ring 14 of the first embodiment, the manipulation ring 14A includes a ring body 141A, a permanent magnet 142, and a pair of O-rings 143 as illustrated in FIG. 6 or 7. Here, the ring body 141A has a length of the center axis direction (rotation axis direction) shorter than that of the ring body 141 of the first embodiment described above. For this reason, the manipulation ring 14A is movable between a first position (FIG. 6) where the manipulation ring 14A abuts on the coupling portion 132 along the rotation axis direction and a second position (FIG. 7) where the manipulation ring 14A abuts on the coupling portion 113 depending on a user manipulation.

In the medical imaging apparatus 5A according to the second embodiment, the function executed by a function execution unit 233A is switched to the first function as the manipulation ring 14A moves to the first position (FIG. 6) in response to a user manipulation. In addition, the function executed by the function execution unit 233A is switched to the second function as the manipulation ring 14A moves to the second position (FIG. 7) in response to a user manipulation.

The medical imaging apparatus 5A according to the second embodiment includes a first Hall element 17A1 and a second Hall element 17A2 instead of the Hall element 17 described in the first embodiment as illustrated in FIG. 6 or 7.

The first Hall element 17A1 has similar configuration and functions to those of the Hall element 17 of the first embodiment described above and is placed to face the permanent magnet 142 moved to the first position (FIG. 6) inside the casing 11. In addition, the first Hall element 17A1 corresponds to a first detection unit according to the disclosure.

The second Hall element 17A2 has similar configuration and functions to those of the Hall element 17 of the first embodiment described above and is placed to face the permanent magnet 142 moved to the second position (FIG. 7) inside the casing 11. In addition, the second Hall element 17A2 corresponds to a second detection unit according to the disclosure.

The medical imaging apparatus 5A according to the second embodiment includes a control unit 23A having a function different from that of the control unit 23 instead of the control unit 23 of the first embodiment described above as illustrated in FIG. 6 or 7.

As illustrated in FIG. 6 or 7, the control unit 23A does not include the function switch unit 231 in comparison with the control unit 23 of the first embodiment described above and includes a manipulation calculation unit 232A and a function execution unit 233A instead of the manipulation calculation unit 232 and the function execution unit 233.

The manipulation calculation unit 232A includes a comparator unit 2321, and first and second manipulation calculation units 2322 and 2323.

The comparator unit 2321 compares signal levels of the analog signals output from the first and second Hall elements 17A1 and 17A2. In addition, the comparator unit 2321 operates only the first manipulation calculation unit 2322 out of the first and second manipulation calculation units 2322 and 2323 if a signal level of the analog signal output from the first Hall element 17A1 is higher than a signal level of the analog signal output from the second Hall element 17A2. Otherwise, if a signal level of the analog signal output from the second Hall element 17A2 is higher than a signal level of the analog signal output from the first Hall element 17A1, the comparator unit 2321 operates only the second manipulation calculation unit 2323 out of the first and second manipulation calculation units 2322 and 2323.

The first manipulation calculation unit 2322 calculates the rotation direction and the rotation angle of the manipulation ring 14A based on a detection result of the first Hall element 17A1.

The second manipulation calculation unit 2323 calculates the rotation direction and the rotation angle of the manipulation ring 14A based on a detection result of the second Hall element 17A2.

Note that the method of calculating the rotation direction and the rotation angle of the manipulation ring 14A using the first and second manipulation calculation units 2322 and 2323 is similar to the method of calculating the rotation direction and the rotation angle of the manipulation ring 14 using the manipulation calculation unit 232 of the first embodiment described above.

The function execution unit 233A executes the first function depending on the rotation direction and the rotation angle of the manipulation ring 14A calculated by the first manipulation calculation unit 2322. In addition, the function execution unit 233A executes the second function depending on the rotation direction and the rotation angle of the manipulation ring 14A calculated by the second manipulation calculation unit 2323.

According to the second embodiment described above, it is possible to obtain the effects similar to those of the first embodiment as described above.

In the medical imaging apparatus 5A according to the second embodiment, the function of the function switch unit according to the disclosure is provided in the manipulation ring 14A. For this reason, it is possible to omit the manipulation receiving unit 15, the through-hole 1121, and the first hermetic connector 16 and improve airtightness of the casing 11.

However, when the first and second positions are close to each other, the first Hall element 17A1 detects a magnetic field of the permanent magnet 142 even by moving the manipulation ring 14A to the second position. Meanwhile, since the second Hall element 17A2 is close to the permanent magnet 142, the signal level of the analog signal output from the second Hall element 17A2 is higher than the signal level of the analog signal output from the first Hall element 17A1.

Here, the medical imaging apparatus 5A according to the second embodiment includes the comparator unit 2321 described above. For this reason, even in the aforementioned case, it is possible to employ the analog signal output from the second Hall element 17A2 instead of the analog signal output from the first Hall element 17A1 in order to calculate the rotation direction and the rotation angle of the manipulation ring 14A.

Therefore, while miniaturization is facilitated by shortening the length of the center axis direction of the casing 11 by reducing a distance between the first and second positions, in the aforementioned case, it is possible to reliably switch the function executed by the function execution unit 233A to the second function and appropriately calculate the rotation direction and the rotation angle of the manipulation ring 14A. Note that this similarly applies to a case where the manipulation ring 14A is moved to the first position.

Third Embodiment

Next, a third embodiment will be described.

In the following description, like reference numerals denote like elements as in the first embodiment, and they will not be described repeatedly.

Figure 8:
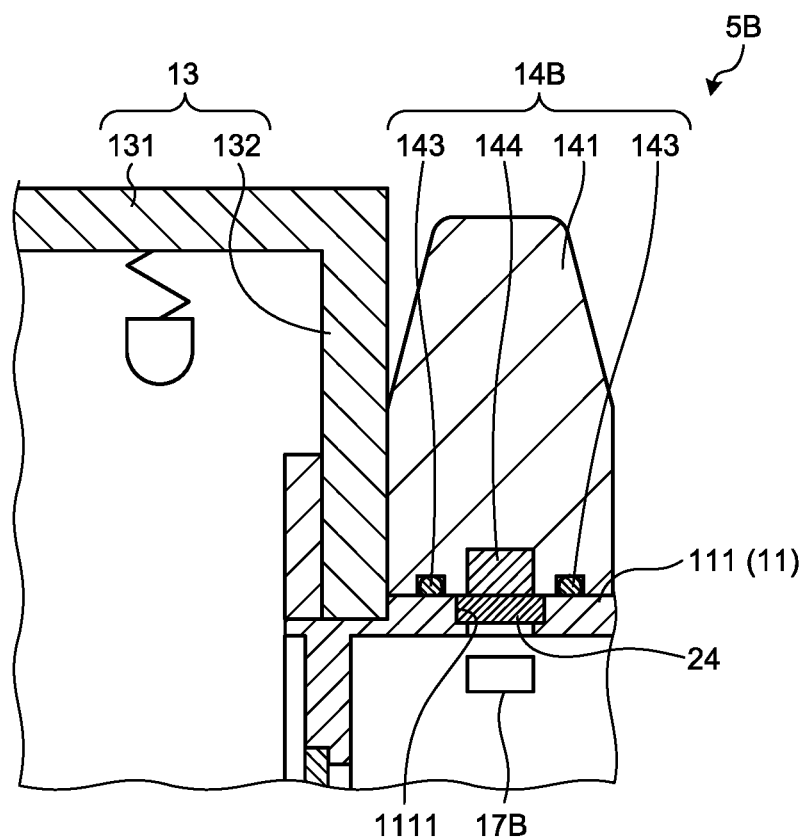
FIG. 8 is a cross-sectional view illustrating a schematic configuration of a medical imaging apparatus according to a third embodiment.

FIG. 8 is a cross-sectional view illustrating a schematic configuration of a medical imaging apparatus 5B according to the third embodiment.

In the medical imaging apparatus 5 of the first embodiment described above, the rotation of the manipulation ring 14 is magnetically detected using the permanent magnet 142 and the Hall element 17.

In comparison, in the medical imaging apparatus 5B according to the third embodiment, the rotation of a manipulation ring 14B is optically detected.

Specifically, the manipulation ring 14B according to the third embodiment includes a reflection ring 144 provided in the manipulation ring 14 of the first embodiment described above instead of the permanent magnet 142 as illustrated in FIG. 8.

The reflection ring 144 is formed in a ring shape having an outer size substantially equal to an inner size of the ring body 141 and is mounted to the inner circumferential surface of the ring body 141. Although not illustrated specifically, "white" reflective plates having a high light reflectivity and "black" reflective plates having a low light reflectivity are alternately arranged along a circumferential direction on an inner circumferential surface of the reflection ring 144.

In the medical imaging apparatus 5B according to the third embodiment, an optical sensor 17B is employed instead of the Hall element 17.

The optical sensor 17B is a part that detects the rotation of the manipulation ring 14B and corresponds to a detection unit according to the disclosure. The optical sensor 17B is placed to face the reflection ring 144 inside the casing 11 as illustrated in FIG. 8.

Here, in the casing 11 (first tubular portion 111), a through-hole 1111 penetrating the first tubular portion 111 is formed in a position facing the optical sensor 17B. In addition, an optical element 24 such as transmissive sapphire glass is fixed to the through-hole 1111 by brazing. That is, the through-hole 1111 is sealed with the optical element 24 in an airtight manner.

Although not illustrated specifically, the optical sensor 17B includes a light-projecting element that projects light onto an inner circumferential surface (reflective plate) of the reflection ring 144 through the optical element 24 and a light-receiving element that receives light reflected from the reflective plate in order to output an analog signal depending on the received light amount. Note that, similarly to the Hall element 17 of the first embodiment described above, the optical sensor 17B outputs two-phase signals (analog signals) having different phases in order to calculate the rotation direction of the manipulation ring 14B. The optical sensor 17B may include a single sensor that outputs the two-phase signals or may include two sensors including a sensor that outputs one of the two-phase signals and a sensor that outputs the other signal. When the optical sensor 17B includes two sensors, the two sensors are respectively arranged, for example, in a position where light may be simultaneously projected onto the reflective plates having the same color and a position where light may be simultaneously projected onto the reflective plates having different colors.

Note that the signal (analog signal) output from the optical sensor 17B is similar to the signal (analog signal) output from the Hall element 17 of the first embodiment described above. For this reason, a method of calculating the rotation direction and the rotation angle of the manipulation ring 14B is similar to that of the first embodiment described above.

Similarly to the third embodiment described above, it is possible to obtain the effects similar to those of the first embodiment described above even when the configuration for optically detecting rotation of the manipulation ring 14B is employed.

Fourth Embodiment

Next, a fourth embodiment will be described.

In the following description, like reference numerals denote like elements as in the first embodiment, and they will not be described repeatedly.

FIG. 9 is a cross-sectional view illustrating a schematic configuration of a medical imaging apparatus 5C according to the fourth embodiment.

In the medical imaging apparatus 5 of the first embodiment described above, the manipulation receiving unit 15 is a push button switch.

In comparison, in the medical imaging apparatus 5C according to the fourth embodiment, a manipulation receiving unit 15C including an optical sensor is employed instead of the manipulation receiving unit 15 as illustrated in FIG. 9. In addition, in the medical imaging apparatus 5C, the through-hole 1121 and the first hermetic connector 16 of the first embodiment described above are omitted.

The manipulation receiving unit 15C is provided inside the casing 11.

Here, a through-hole 1122 penetrating the second tubular portion 112 is formed to face the manipulation receiving unit 15C in the casing 11 (second tubular portion 112). In addition, an optical element 25 such as transmissive sapphire glass is fixed to the through-hole 1122 by brazing. That is, the through-hole 1122 is sealed with the optical element 25 in an airtight manner.

Although not illustrated specifically, the manipulation receiving unit 15C includes a light-receiving element that receives light to output an analog signal depending on the received light amount. That is, when the optical element 25 is covered by a user's finger or the like, the manipulation receiving unit 15C outputs an analog signal corresponding to a small amount of the receiving light. Meanwhile, when the optical element 25 is not covered, the manipulation receiving unit 15C outputs an analog signal corresponding to a large amount of the receiving light.

The function switch unit 231 according to the fourth embodiment switches the function executed by the function execution unit 233 to the first function, for example, when the analog signal corresponding to a small amount of the receiving light is output from the manipulation receiving unit 15C (when the optical element 25 is covered by a user's finger or the like). Meanwhile, when the analog signal corresponding to a large amount of the receiving light is output from the manipulation receiving unit 15C (when the optical element 25 is not covered), the function switch unit 231 switches the function executed by the function execution unit 233 to the second function.

Alternatively, similarly to the optical sensor 17B of the third embodiment described above, the manipulation receiving unit 15C may include a light-transmitting element in addition to the light-receiving element.

According to the fourth embodiment described above, it is possible to obtain the following effects in addition to the effects of the first embodiment described above.

In the medical imaging apparatus 5C according to the fourth embodiment, the manipulation receiving unit 15C including an optical sensor is employed. For this reason, a user may simply cover the optical element 25 with a finger or not in order to perform a manipulation for changing the function executed by the function execution unit 233 between the first or second function. Therefore, it is possible to improve manipulability.

Other Embodiments

While the embodiments of the disclosure have been described hereinbefore, the disclosure is not limited by the first to fourth embodiments described above.

In the first to fourth embodiments described above, the first and second functions are not limited to those described in the first embodiment (such as focus adjustment and exposure adjustment). For example, in addition to the focus adjustment and the exposure adjustment, adjustment of an angle of view of the lens unit 18 (zoom adjustment of the subject image), adjustment of calculation parameters for image processing (such as brightness adjustment) for an image signal (digital signal) output from the imaging unit 21, or the like may also be employed as the first and second functions.

Although two functions, that is, the first and second functions are employed as the function executed by the manipulation ring 14 (14A and 14B) in the first to fourth embodiments described above, three or more functions may also be employed without a limitation.

At least part of the configuration provided in the medical imaging apparatus 5 (5A to 5C) of the first to fourth embodiments described above may also be provided inside the insertion unit 2. In addition, the insertion unit 2 may be a flexible endoscope instead of the rigid endoscope.

At least a part of the functions of the control unit 23 (23A) of the first to fourth embodiments described above may be provided outside of the medical imaging apparatus 5 (5A to 5C) (such as the connectors CN1 and CN2 and the control device 9).

Although the medical imaging apparatus according to the disclosure is employed in the endoscope in the first to fourth embodiments described above, the disclosure is not limited thereto. The medical imaging apparatus according to the disclosure may be employed in a microscopic unit of a surgery microscope that enlargedly captures a predetermined view field area inside of a subject (in vivo) or on a surface of the subject (on a surface of a living body) (for example, see JP 2016-42981 A).

In the medical imaging apparatus according to the disclosure, when the function switch unit switches the function executed by the function execution unit to a first function, the function execution unit executes the first function (for example, focus adjustment) depending on the rotation direction and the rotation angle of the manipulation ring calculated by the manipulation calculation unit as the manipulation ring is rotated. In addition, when the function switch unit switches the function executed by the function execution unit to a second function, the function execution unit executes the second function (for example, exposure adjustment) depending on the rotation direction and the rotation angle of the manipulation ring calculated by the manipulation calculation unit as the manipulation ring is rotated. That is, at least two functions (for example, focus adjustment and exposure adjustment) may be executed using a single manipulation ring.

Therefore, since it is not necessary to provide a plurality of manipulation rings, it is possible to facilitate miniaturization and reduce a weight of the medical imaging apparatus. In addition, since at least two functions are executed by the manipulation ring, it is possible to perform delicate adjustment and improve convenience.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical imaging apparatus, comprising:
a casing that forms an exterior;
an imaging sensor housed in the casing and configured to capture a subject image;
a single manipulation ring rotatably provided on an outer surface of the casing; and
control circuitry configured to
detect rotation of the single manipulation ring;
calculate a rotation direction and a rotation angle of the single manipulation ring based on a detection result;
execute a first function or a second function depending on the rotation direction and the rotation angle of the single manipulation ring calculated, wherein the first function is a different type of adjustment than the second function; and
switch a function executed by the control circuitry to the first function or the second function.

2. The medical imaging apparatus according to claim 1, further comprising a user input to receive a user manipulation, and
wherein the control circuitry is further configured to switch the function executed by the control circuitry to the first function or the second function depending on a user manipulation of the user input.

3. The medical imaging apparatus according to claim 2, wherein the user input is a push button switch on an outer surface of the casing.

4. The medical imaging apparatus according to claim 2, wherein the user input is an optical sensor provided inside the casing to detect whether or not an opening formed in the casing is covered.

5. The medical imaging apparatus according to claim 1, wherein the single manipulation ring is movable to a first position or a second position along a rotation axis direction of the single manipulation ring,
the control circuitry is further configured to switch the function executed by the control circuitry to the first function when the single manipulation ring moves to the first position, and switch the function executed by the control circuitry to the second function when the single manipulation ring moves to the second position.

6. The medical imaging apparatus according to claim 5, further comprising:
  a first detector to detect rotation of the single manipulation ring moved to the first position, and
  a second detector to detect rotation of the single manipulation ring moved to the second position,
  the control circuitry is further configured to
    calculate a rotation direction and a rotation angle of the single manipulation ring based on a detection result of the first detector as a first calculation, and
    calculate a rotation direction and a rotation angle of the single manipulation ring based on a detection result of the second detector as a second calculation, and
  execute the first function depending on the rotation direction and the rotation angle of the single manipulation ring of the first calculation and execute the second function depending on the rotation direction and the rotation angle of the single manipulation ring of the second calculation.

7. The medical imaging apparatus according to claim 6, wherein the first and second detectors are to output analog signals depending on the detection result, and
  the control circuitry is further configured to compare signal levels of the analog signals output from the first and second detectors to calculate only one of the first and second calculations corresponding to the detector having a higher signal level.

8. The medical imaging apparatus according to claim 1, wherein the first function is a focus adjustment and the second function is an exposure adjustment.

9. The medical imaging apparatus according to claim 8, wherein the exposure adjustment includes adjusting an iris.

10. A method of controlling an optical image output from an imaging sensor in a medical imaging apparatus using a manipulation single ring, the method comprising:
  detecting rotation of the single manipulation ring;
  calculating a rotation direction and a rotation angle of the single manipulation ring based on a detection result;
  executing a first function or a second function depending on the rotation direction and the rotation angle of the single manipulation ring calculated, wherein the first function is a different type of adjustment than the second function; and
  switching a function executed to the first function or the second function.

11. The method according to claim 10, wherein the first function is a focus adjustment and the second function is an exposure adjustment.

12. The method according to claim 11, wherein the exposure adjustment includes adjusting an iris.

* * * * *